US00RE39282E

(19) United States
(12) Reissued Patent
Larder et al.

(10) Patent Number: US RE39,282 E
(45) **Date of Reissued Patent: *Sep. 12, 2006**

(54) NUCLEIC ACID DERIVATIVES

(75) Inventors: Brendan A. Larder, Cambridgeshire (GB); Sharon D. Kemp, Cambridgeshire (GB)

(73) Assignee: SmithKline Beecham Corporation, Philadelphia, PA (US)

( * ) Notice: This patent is subject to a terminal disclaimer.

(21) Appl. No.: 10/293,219

(22) Filed: Nov. 12, 2002

Related U.S. Patent Documents

Reissue of:
(64) Patent No.: 5,409,810
Issued: Apr. 25, 1995
Appl. No.: 07/984,255
Filed: Dec. 1, 1992

U.S. Applications:
(63) Continuation of application No. 08/839,010, filed on Apr. 23, 1997, now Pat. No. Re. 37,918, which is a continuation of application No. 07/564,062, filed on Aug. 8, 1990, now abandoned.

(30) Foreign Application Priority Data

Aug. 9, 1989 (GB) ..... 8918226

(51) Int. Cl.

| | |
|---|---|
| ***C12Q 1/70*** | (2006.01) |
| ***C12Q 1/68*** | (2006.01) |
| ***C12P 19/34*** | (2006.01) |
| ***G01N 33/00*** | (2006.01) |
| ***C07H 21/04*** | (2006.01) |

(52) U.S. Cl. ..... 435/5; 435/6; 435/91.1; 435/91.32; 435/183; 435/193; 436/501; 436/94; 536/23.72; 536/24.33

(58) Field of Classification Search ..... 435/5, 435/70.21, 91.1, 91.2, 91.33, 91.51, 974, 435/6, 91.32, 183, 193, 235.1, FOR. 203; 536/23.72, 24.32, 24.33, 25.3; 436/501, 94
See application file for complete search history.

(56) References Cited

U.S. PATENT DOCUMENTS 5,409,810 A * 4/1995 Larder et al. ..... 435/5
RE37,918 E * 12/2002 Larder et al. ..... 435/5

FOREIGN PATENT DOCUMENTS

EP 229701 AO 7/1987

OTHER PUBLICATIONS

Journal of Infectious Diseases, vol. 149, No. 3, 1984, 298–310.*
Cell, vol. 40, 1985, 9–17.*
Nature, vol. 313, 1985, 277–284.*
Science, vol. 229, 1985, 563–566.*
Science, vol. 233, 1986, 1076–1078.*
Proceedings of the National Academy of Sciences, USA, 1986, vol. 83, 8333–8337.*
Nature, vol. 324, 1986, 163–166.*
Nature, vol. 327, 1987, 293–297.*
J. of Virology, vol. 61, No. 5, 1987, 1690–1694.*
Nucleic Acids Research, vol. 15, No. 13, 1987, 5373–5390.*
Proceedings of the National Academy of Sciences, USA, vol. 84, 1987, 4974–4978.*
Nature, vol. 330 1987, 384–386.*
Science, vol. 239, 1988, 295–297.*
Science, vol. 239, 1988, 487–491.*

(Continued)

*Primary Examiner*—Bradley L. Sisson
(74) *Attorney, Agent, or Firm*—Townsend and Townsend and Crew, LLP

(57) ABSTRACT

This invention relates to a methodology for assessing the sensitivity of an HIV-1 sample to zidovudine and to diagnostic assays for use in such assessment.

24 Claims, 7 Drawing Sheets

OTHER PUBLICATIONS

The Lancet, 10.9.88, 596–599.*
JAMA, vol. 7, No. 15, 1988, 2236–2239.*
DNA, vol. 7, No. 4, 1988, 287–295.*
Journal of Infectious Diseases, vol. 158, No. 6, 1988, 1158–1169.*
Journal of Infectious Diseases, vol. 158, No. 6, 1988, 1170–1176.*
Proceedings of the National Academy of Sciences, USA, vol. 86, 1989, 232–236.*
Journal of Virology, 1989, vol. 63, No. 1, 64–75.*
Science, vol. 243, 1731–1734.*
Nucleic Acids Research, vol. 17, No. 7, 1989, 2503–2516.*
Proceedings of the National Academy of Sciences, USA, vol. 86, 1989, 2423–2427.*
Clinical Microbiology Reviews, vol. 2, No. 2, 1989, 217–226.*
Analytical Biochemistry, vol. 177, 1989, 27–32.*
TIG, vol. 5, No. 6, Jun. 1989, 185–189.*
Science, vol. 246, 1989, 1155–1158.*
Cold Spring Harbour Lab Press, 2nd Edition, Lab Manual "Molecular Cloning."*
Journal of Virology, vol. 64, No. 2, 1990, 864–872.*
Larder et al., Proceedings of the National Academy of Sciences, USA, vol. 86, Jul. 1989, 4803–4807.*
Larder et al., Science, vol. 246, Dec. 1, 1989, 1155–1158.*
Larder et al., Nature, vol. 327, Jun. 25, 1987, 716–717.*
Proceedings of the National Academy of Sciences, USA, vol. 86, Jul. 1989, 4803–4807.*
Nature, vol. 327, Jun. 25, 1987, 716–717.*
AIDS, vol. 5, No. 2, 1991, pp. 137–144, Larder et al., Zidovudine resistance predicted by direct detection of mutations in DNA from HIV—etc.
Analytical Biochemistry, 177, 1989, pp. 27–32.
Cell, vol. 40, 1985, pp. 9–17.
Cold Spring Harbour Lab Press 2nd Ed. Lab Manual "Manual Cloning".
Clinical Mircobiology Reviews, vol. 2, No. 2, 1989, 217–226.
DNA, vol. 7, No. 4, 1988, pp. 287–295.
Larder et al., Int. Conf. AIDS 5, 1989, p. 516, Abstract.
Nature, vol. 330, 1987, pp. 384–386.
Nucleic Acids Research, vol. 17, No. 7, 1989, pp. 2503–2516, Newton et al. Analysis of any point mutation in DNA. The amplification etc. Abstract.
Opposition Statement to EP–B1 0422 762, 12 pages, 1996.
Proc. Nat. Acad. Sci., vol. 88, 1991, pp. 3092–3096, Japour et al., Detection of human . . . RNA hybridization.
Science, vol. 233, 1986, pp. 1076–1078.
Trends in Genetics, vol. 5, No. 6, Jun. 1989, pp. 165–198.
Sommer et al., Minimal homology requirements for PCR primers, Nucleic Acids Research, vol. 17, No. 16, p. 6749.

* cited by examiner

Myers, G. et al., Human Retroviruses and AIDS: A Compilation and Analysis of Nucleic Acid and Amino Acid Sequences (Theoretical and Biophysics, Los Alamos National Laboratory, Los Alamos, NM, pII-22 (1989) amino acid number which is changed (Resdiue #1 of RT - Proline, which is shown in Myers et al)

*Fig. 4B*

Lys 70

← – –3′ TA ACC TCT TTT AAT CAT CTA A 5′ *wt* OLIGO

5′··· (2334) ACT AAA TGG AGA AAA TTA GTA GAT TTC···3′ *wt* DNA

3′CA ACC TCT TTT AAT CAT CTA A 5′ MUTANT OLIGO

3TA ACC TCT TTT AAT CAT CTA A 5′ *wt* OLIGO

5′··· (2334) ACT AGA TGG AGA AAA TTA GTA GAT TTC···3′ MUTANT DNA

← – –3′ CA ACC TCT TTT AAT CAT CTA A 5′ MUTANT OLIGO

Arg 70

NUCLEIC ACID DERIVATIVES

Matter enclosed in heavy brackets [ ] appears in the original patent but forms no part of this reissue specification; matter printed in italics indicates the additions made by reissue.

[This is a continuation of application Ser. No. 07/564,062, filed Aug. 8, 1990, now abandoned.] *The present invention is a continuation of Ser. No. 08/839,010, filed Apr. 23, 1997, now RE 37,918 E, which is a reissue of Ser. No. 07/984,255, filed Dec. 1, 1992, which is a continuation of Ser. No. 07/564,062, filed Aug. 8, 1990, now abandoned, which claims benefit under 35 USC 119 from GB 8918226, filed Sep. 8, 1989.*

The present invention relates to a method for assessing the sensitivity of an HIV-1 sample to zidovudine, and to diagnostic assays for use in such assessment.

One group of viruses which has recently assumed a particular importance are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome is incorporated into the host cell genome, allowing it to take full advantage of the host cell's transcription/translation machinery for the purposes of replication. Once incorporated, the viral DNA is virtually indistinguishable from the host's DNA and, in this state, the virus may persist for as long as the cell lives. As it is believed to be invulnerable to attack in this form, any treatment must be directed at another stage of the virus life cycle and would, have to be continued until all virus-infected cells have died.

A species of retrovirus has also been reproducibly isolated from patients with AIDS and is now named as human immunodeficiency virus (HIV-1) and is also known as human T-cell lymphotropic virus III (HTLV III), AIDS associated retrovirus (ARV), or lymphadenopathy associated virus (LAV).

This virus has been shown preferentially to infect and destroy T-cells bearing the $OKT^4$ surface marker and is now generally accepted as the actiologic agent of AIDS. The patient progressively loses his set of T-cells, upsetting the overall balance of the immune system, reducing his ability to combat other infections and predisposing him to opportunistic infections which frequently prove fatal. Thus, the usual cause of death in AIDS victims is by opportunistic infection, such as pneumonia or virally induced cancers, and not as a direct result of HIV infections.

The complete nucleotide sequence of the AIDS virus HIV-1 or as it was previously known HTLV-III has been elucidated (Ratner, L., et al. Nature, Vol. 313, p 277, 24 Jan. 1985).

Recently, HIV-I has also been recovered from other tissue types, including B-cells expressing the $T^4$ marker, macrophages and non-blood associated tissue in the central nervous system. This infection of the central nervous system has been discovered in patients expressing classical AIDS symptoms and is associated with progressive demyelination, leading to wasting and such symptoms as encephalopathy, progressive dysarthria, ataxia and disorientation. Further conditions associated with HIV infection are the asymptomatic carrier state, progressive generalised lymphadenopathy (PGL) and AIDS-related complex (ARC). HIV-1 can also be present in other tissues or physiological fluids such as urine, plasma, blood, serum, semen, tears, saliva or cerebrospinal fluid.

3'-Azido-3'-deoxythymidine-(hereafter called "zidovudine") is used in the control of HIV infections including AIDS and ARC. Zidovudine is a thymidine analogue whose triphosphate form inhibits the replication of the human immunodeficiency virus (HIV) by competitive binding to viral reverse transcriptase (RT) and DNA chain termination after phosphorylation by cellular enzymes (Furman, P. A et al., Proc. Natl. Acad. Sci. USA, 1986, 83: 8333). It is an effective antiviral agent both in vitro and in vivo against a variety of retroviruses (Mitsuya H et al., Cancer Res., 1987, 47: 2190; Ruprecht R. M et al., Nature, 1986, 323: 476.) and has been demonstrated to improve the quality and length of life of patients with AIDS and advanced ARC (Fischl M. A. et al., N. Engl. J. Med., 1987, 317: 185; Schmitt F. A. et al, N. Engl. J. Med 1988, 319: 1573; Greagh-Kirk T et al, J. Am. Med. Assoc., 1988, 260.: 3009) and also in asymptomatics with low $CD_4^+$ cell levels.

As with any anti-infective agent, concern about the potential development of resistance has engendered extensive investigations evaluating factors which might potentially alter the sensitivity of retroviruses to zidovudine.

A study carried out to measure zidovudine sensitivity of HIV isolates from patients with AIDS or ARC after zidovudine treatment has in fact revealed that a number of isolates from patients treated for six months or more showed reduced sensitivity to zidovudine whereas isolates from untreated individuals and those treated for less than six months showed uniform sensitivity to the drug (Larder, B. A., Darby, G, and Richman, D. D., Science, Vol. 243, 1731, 31st Mar. 1989).

At present the way to determine the sensitivity of HIV-1 strains to zidovudine is to isolate HIV-1 from a patient's peripheral blood lymphocytes. HIV-1 isolates can be made by co-cultivation of peripheral blood lymphocytes (PBL's) with cells of the continuous line MT-2. (Harada, S., Koyanagt, Y., Yamamoto, N., Science 229, 563 (1985). This procedure can take anything from between four and fourteen days before HIV-1 can be isolated. The diagnosis of resistant strains of HIV-1 relies firstly on the isolation of virus and then on sensitivity testing by a tissue culture method and so is consequently extremely slow.

The present inventors have discovered the basis for resistance of HIV-1 to zidovudine at the nucleic acid level. Five nucleotide substitutions have been identified in the HIV-1 genome which result in a change of four amino acids in the RT protein. This discovery has important implications for the detection of resistant HIV isolates because of the highly conserved nature of these nucleotide mutations in RT conferring resistance to zidovudine, and opens the way to the routine detection of such resistant isolates.

It is possible to carry out a diagnostic assay for the screening of bodily samples from patients for an assessment of the sensitivity of HIV-I to zidovudine. Using the knowledge of the mutations identified as important in the development of highly resistant strains of HIV-1 such an assay can be developed.

An analysis of a group of resistant mutants was carried out by nucleotide sequencing which allowed the identification of mutations in the HIV RT gene that confer resistance to zidovudine. The complete RT coding region (1.7 kb) was obtained for each isolate using polymerase chain reaction (PCR) amplification of infected cell DNA. The nucleotide changes at the five positions in HIV-1 RT that confer resistance to zidovudine are illustrated in FIG. 1. Numbering of the nucleotides of the HIV-1 RT gene is as reported by Ratner et al (Ratner et al., Nature, 313, 277, (1985)).

It is demonstrated that these specific mutations confer zidovudine-resistance, as an infectious molecular HIV clone containing only these nucleotide changes is resistant to zidovudine. (See Example 4).

From analysis of clinical samples it appears that the sensitivity of HIV-1 to zidovudine changes over a period of time. It appears that mutations may occur at any of one or more of the five identified sites as the time from the onset of treatment with zidovudine advances and it is clear than an HIV-1 sample which carries all five mutations is highly resistant to zidovudine.

At this time it is not possible to predict any order of occurrence of these mutations, although particular attention is being focussed on the two nucleotides of the wild-type DNA sequence (or its corresponding RNA) or to the two nucleotides of the mutant DNA sequence (or its corresponding RNA) set forth in FIG. 1 at the 2772- and 2773-positions.

According to a first aspect of the invention there is provided a method for assessing the sensitivity of an HIV-1 sample to zidovudine, which comprises:

(i) isolating nucleic acid from the sample, (ii) hybridising an oligonucleotide to the nucleic acid, the oligonucleotide being complementary to a region of the wild-type DNA sequence (or its corresponding RNA) or to a region of the mutant DNA sequence set forth in FIG. 1 (or its corresponding RNA) and terminating at the 3'-end with the nucleotide in the 2328-, 2338-, 2772-, 2773- or 2784-position, (iii) attempting polymerization of the nucleic acid from the 3' end of the oligonucleotide, (iv) ascertaining whether or not an oligonucleotide primer extended product is present.

It is possible to use genomic DNA or RNA isolated from HIV-1 samples in this methodology. Suitable cells for supporting the growth of HIV-1, such as MT-2 cells, are firstly infected with an HIV-1 isolate and incubated for a period of time. The cells are recovered by centrifugation. DNA can then be isolated by digestion of the cells with proteinase K in the presence of EDTA and a detergent such as SDS, followed by extraction with phenol (see Example 1 for the methodology used by the inventors for the isolation of HIV-1 DNA).

Well-known extraction and purification procedures are available for the isolation of RNA from a sample. RNA can be isolated using the following methodology. Suitable cells are again infected and incubated for a period of time. The cells are recovered by centrifugation. The cells are resuspended in an RNA extraction buffer followed by digestion using a proteinase digestion buffer and digestion with proteinase K. Proteins are removed in the presence of a phenol/chloroform mixture. RNA can then be recovered following further centriguation steps. (Maniatis, T., et al, Molecular Coning, A Laboratory Manual, 2nd Edition, Cold Spring Harbor Laboratory Press, (1989)).

Although it is possible to use unamplified nucleic acid, due to the relative scarcity of nucleic acid in an HIV-1 sample it is preferably to amplify it. Nucleic acid may be selectively amplified using the technique of polmerase chain reaction (PCR), which is an in vitro method for producing large amounts of a specific nucleic acid fragment of defined length and sequence form small amounts of a template.

The PCR is comprised of standard reactants using $Mg^{2+}$ concentration, oligonucleotide primers and temperature cycling conditions for amplification of the RT gene using the primers. The primers are chosen such that they will amplify the entire RT gene or a selected sequence which incorporates nucleotides corresponding to a region of the wild-type DNA sequence of HIV-1 between the nucleotides at the 2328- and 2784-positions set forth in FIG. 1. Example 2 provides a description of PCR used to amplify target nucleic acid.

RNA cannot be amplified directly by PCR. Its corresponding cDNA must be first of all synthesised. Synthesis of cDNA is normally carried out by primed reverse transcription using oligo-dT primers. Advantageously, primers are chosen such that they will amplify the nucleic acid sequence for RT or a selected sequence which incorporates nucleotides corresponding to the region of RNA corresponding to the wild-type DNA sequence or to the region of the mutant DNA sequence set forth in FIG. 1 between the nucleotides 2328- and 2784-. This could be achieved by preparing an oligonucleotide primer which is complementary to a region of the RNA strand which is up-stream of the corresponding sequence of the wild-type DNA sequence between nucleotides 2328- and 2784-. cDNA prepared by this methodology (see Maniatis, T., et al., supra.) can then be used in the same way as for the DNA already discussed.

The next stage of the methodology is to hybridise to the nucleic acid an oligonucleotide which is complementary to a region of the wild-type DNA sequence (or its corresponding RNA) or to a region of the mutant DNA sequence (or its corresponding RNA) set forth in FIG. 1 and terminating at the 3'- end with the nucleotide at the 2328-, 2338-, 2772-, 2773- or 2784- position.

Conditions and reagents are then provided to permit polymerisation of the nucleic acid from the 3'-end of the oligonucleotide primer. Such polymerisation reactions are well-known in the art.

If the oligonucleotide primer has at its 3'-end a nucleotide which is complementary to a mutant genotype, that is a genotype which has a nucleotide change at the 2328-, 2338-, 2772-, 2773- or 2784- positions as set forth in FIG. 1 then polymerization of the nucleic acid sequence will only occur if the nucleic acid of the sample is the same as the mutant genotype. Polymerisation of a wild type nucleic acid sequence will not occur or at least not to a significant extent because of a mis-match of nucleotides at the 3'- end of the oligonucleotide primer and the nucleic acid sequence of the sample.

If the oligonucleotide primer has at its 3'-end a nucleotide which is complementary to the wild-type genotype, that is a genotype which has the wild-type nucleotide at the corresponding 2328-, 2338-, 2772-, 2773- or 2784- position as set forth in FIG. 1, then there will be polymerisation of a nucleic acid sequence which is wild-type at that position. There will be no polymerisation of a nucleic acid which has a mutant nucleotide at the 3'-position.

The preferred length of each oligonucleotide is 15–20 nucleotides. The oligonucleotide can be prepared according to methodology well known to the man skilled in the art (Koster, H., Drug Research, 30 p548 (1980); Koster, H., Tetrahedron Letters p1527 (1972); Caruthers, Tetrahedron Letters, p719, (1980); Tetrahedron Letters, p1859, (1981); Tetrahedron Letters 24, p245, (1983); Gate, M., Nucleic Acid Research, 8 p1081, (1980)) and is generally prepared using an automated DNA synthesiser such as an Applied Biosystems 381A synthesiser.

It is convenient to determine the presence of an oligonucleotide primer extended product. The means for carrying out the detection is by using an appropriate label.

The label may be conveniently attached to the oligonucleotide primer or to some other molecule which will bind the primer extended polymerisation product.

The label may be for example an enzyme, radioisotope or fluorochrome. A preferred label may be biotin which could be subsequently detected using streptavidin conjugated to an enzyme such as peroxidase or alkaline phosphatase. The presence of an oligonucleotide primer extended polymerisation product can be detected for example by running the polymerisation reaction on an agarose gel and observing a specific DNA fragment labelled with ethidium bromide, or Southern blotted and autoradiographed to detect the presence or absence of bands corresponding to polymerised product. If a predominant band is present which corresponds only to the labelled oligonucleotide then this indicates that polymerisation has not occurred. If bands are present of the correct predicted size, this would indicate that polymerisation has occurred.

For example, DNA isolated from patients' lymphocytes as described herein is used as a template for PCR amplification using synthetic oligonucleotide primers which either match or mis-match with the amplified sequences. The feasibility of PCR in detecting such mutations has already been demonstrated. PCR using the Amplification Refractory Mutation system ("ARMS") (Newton, C. R., et a. Nucleic Acids Research, 17, p.2503, (1989)) Synthetic oligonucleotides are produced that anneal to the regions adjacent to and including the specific mutations such that the 3' end of the oligonucleotide either matches or mismatches with a mutant or wild-type sequence. PCR is carried out which results in the identification of a DNA fragment (using gel electrophoresis) where a match has occurred or no fragment where a mismatch occurred.

For example, using the 2 oligonucleotides below as PCR primers:

5'-ATG TTT TTT GTC TGG TGT GGT-3'- (1) OR

5'-ATG TTT TTT GTC TGG TGT GAA-3'- (2)

plus the common oligonucleotide primer:

"B"-5'- GGA TGG AAA GGA TCA CC-3' it is possible to distinguish between sensitive and resistant virus. DNA is extracted from HIV-1 infected T-cells as described herein and subjected to "ARMS" PCR analysis using these primers. If the virus is sensitive a 210 bp fragment is generated with oligonucleotide B+(1) but not with B+(2). By contrast, if the virus is zidovudine resistant a 210 bp fragment is generated with B+(2) but not with B+(1).

The presence of a fragment is identified by using an oligonucleotide primer as described above, i.e. by attempting polymerisation using an oligonucleotide primer which may be labelled for the amplified DNA fragment under stringent conditions which only allow hybridisation of complementary DNA (the only difference is that differential hybridisation does not have to be performed as fragments of DNA amplified by the "ARMS" method will be the same whether derived from mutant or wild-type DNA, so a common oligonucleotide can be used to detect the presence of these fragments. The sequence of such an oligonucleotide is derived from a DNA sequence within the DNA fragment that is conserved amongst HIV-1 strains).

The above PCR assay may be adapted to enable direct detection of mutations associated with zidovudine resistance in DNA from PBL samples from infected individuals that have not been cultured to obtain virus. As this material generally contains considerably less HIV-1 DNA than that in infected lymphoid cultures a "double PCR" (or nested set) protocol can be used (Simmonds, P., Balfe, P. Peutherer, J. F., Ludlam, C. A., Bishop, J. O. and Leigh Brown, A. J., J. Virol., 64, 864–872, (1990)) to boost the amount of target HIV-1 RT DNA signal in the samples. The double PCR overcomes the problem of limited amplification of a rare template sequence. Initially a fragment may be amplified from within the RT region which encompasses all the commonly observed mutations. A small amount of the pre-amplified material may be used in the second PCR with primer pairs designed to allow discrimination of wild type and mutant residues.

A suitable test kit for use in an assay to determine the resistance status of an HIV-1 sample to zidovudine which makes use of a methodology according to the first aspect of the invention, comprises an oligonucleotide being complementary to a region of the wild-type DNA sequence (or its corresponding RNA) or to a region of the mutant DNA sequence set forth in FIG. 1 (or its corresponding RNA) and terminating at the 3'-end with the nucleotide in the 2328-, 2338-, 2772-, 2773- or 2784- position, other materials required for polymerisation of the nucleic acid from the 3'-end of the oligonucleotide and means for determining the presence of an oligonucleotide primer extended product. Such other materials include appropriate enzymes, buffer and washing solutions, and a label and a substrate for the label if necessary. If PCR is used to amplify nucleic acid then additional materials such as appropriate oligonucleotide primers which will amplify a region of the wild-type DNA sequence (or its corresponding RNA) or a region of the mutant DNA sequence set forth in FIG. 1 (or its corresponding RNA) containing one or more of the nucleotides at the 2328-, 2338-, 2772-, 2772- or 2784- position, appropriate enzymes and dNTP's should be included.

In a second aspect of the invention there is provided a method for determining the sensitivity of an HIV-1 sample to zidovudine which comprises:

(i) isolating the nucleic acid from the sample, (ii) hybridising the nucleic acid with an oligonucleotide being complementary to a region of the wild-type DNA sequence (or its corresponding RNA) or to a region of the mutant DNA sequence set forth in FIG. 1 (or its corresponding RNA) containing one or more of the nucleotides at the corresponding 2328-, 2338-, 2772-, 2773- and/or 2784- position, (iii) ascertaining whether or not any of the resulting hybrids of the oligonucleotide and nucleic acid have complementary nucleotides at one of these positions.

Preferably the oligonucleotide is so designed to form a perfectly matched hybrid with its complement.

Nucleic acid (DNA or RNA) is isolated from a sample by the aforementioned methods as described for the first aspect of the invention.

Similarly, PCR may be used to amplify the RT DNA (or its corresponding RNA) or preferably to amplify a region of the RT DNA (or its corresponding RNA) which incorporates DNA (or its corresponding RNA) containing one or more of the nucleotides at the 2328-, 2338-, 2772-, 2775- and/or 2784- position (see Example 2).

In the second stage of this methodology the nucleic acid is then used to hybridise to oligonucleotides complementary to a region of the wild-type DNA sequence (or its corresponding (RNA) or to a region of the mutant DNA sequence set forth in FIG. 1 (or its corresponding RNA) containing one or more of the nucleotides at the aforementioned positions.

The oligonucleotide may be of any length depending on the number of nucleotide positions of interest which are being examined. If the oligonucleotide is designed to include a nucleotide at only one position of interest then this nucleotide is preferably at or close to the centre position of the oligonucleotide.

For example, referring to FIG. 1, one oligonucleotide probe for detection of the mutation at nucleotide 2328- would be complementary to the mutated RT gene sequence and would include at its nucleotide corresponding to nucleotide 2328- the nucleotide complementary to the mutated 2328- nucleotide. A second oligonucleotide probe for the wild type HIV-1 RT would include at its nucleotide corresponding to nucleotide 2328- the nucleotide complementary to the wild-type 2328- nucleotide. Oligonucleotide probes designed to detect one or more of the mutations referred to in FIG. 1 are used to detect a specific mutation or that there has been a mutation.

In order to ascertain whether or not the oligonucleotide and nucleic acid sequence have formed a matched hybrid, specific hybridisation conditions are set so that a hybrid is only formed when the nucleotide or nucleotides at one or more of the 2328-, 2338-, 2772-, 2773- and 2784- position is or are complementary to the corresponding nucleotide or nucleotides of the oligonucleotide which either permits hybridisation or no hybridisation. It is important to establish for example the temperature of the reaction and the concentration of salt solution before carrying out the hybridisation step to find conditions that are stringent enough to guarantee specificity (Maniatis, T., et al., Molecular Cloning, A Laboratory Manual, 2nd edition, Cold Spring Harbour laboratory Press, (1989)). If the oligonucleotide probe has a DNA sequence which is complementary to a wild-type nucleic acid sequence at one or more of its nucleotides corresponding to the 2328-, 2338-, 2772-, 2773- or 2784- position of the DNA sequence of FIG. 1 then this oligonucleotide will hybridise perfectly to wild-type nucleic acid. If there is no hybridisation then this would suggest that the nucleic acid isolated from the sample contains one or more mutations.

If the oligonucleotide probe has a DNA sequence which is complementary to a mutant nucleic acid sequence at one or more of its nucleotides corresponding to the 2328-, 2338-, 2772-, 2773- or 2784- positions of the DNA sequence of FIG. 1 then this oligonucleotide will hybridise perfectly to mutant nucleic acid. If there is no hybridisation this would suggest that the nucleic acid isolated from the sample contains no such mutation or mutations. The oligonucleotide probes may be labelled as a means of detection as for the first aspect of the invention.

The hybridisation and subsequent removal of non-hybridised nucleic acids are performed under stringent conditions which only allow hybridisation of the complementary DNA and not the oligonucleotide containing a mismatch (i.e. oligonucleotide specific hybridisation as described for the detection of sickle cell mutation using the β-globin or HLA-DQα gene (Saikt, R. K., et al., Nature, 324, p163, (1986)), the activated Ras gene (Ver Laan-de, Vries, M., et al., Gene, 50, 313, (1986)) and β-thalassaemia Wong, C., et al., Nature, 330, p384, (1987)).

The hybridisation may be carried out by immobilisation of the RT nucleic acid sequence onto nitrocellulose, nylon or other solid matrix (eg. dot-blot). It is convenient to determine the presence of an hybrid by using the means of a label. For example, the chemically synthesised oligonucleotide probes can be suitably labelled using enzyme, radiosotope or fluorochrome. A preferred label may be biotin which could be subsequently detected using streptavidin conjugated to an enzyme such as peroxidase or alkaline phosphatase.

Alternatively the hybridisation may be carried out by immobilisation of the chemically synthesised oligonucleotides referred to above, which are unlabelled, onto a solid support referred to above and subsequently hybridisation by a labelled RT nucleic acid sequence as described previously.

In both situations described above for hybridisation suitable control reactions will be incorporated to determine that efficient hybridisation has occurred. (eg the hybridisation of oligonucleotides to a complementary oligonucleotide).

Results would be readily interpreted as the isolated nucleic acid would hybridise to either the wild type oligonucleotide or the mutant oligonucleotide.

A suitable test kit for use in an assay to determine the sensitivity of an HIV-1 sample to zidovudine which makes use of a methodology according to the second aspect of the invention comprises an oligonucleotide being complementary to a region of the wild-type DNA sequence (or its corresponding RNA) or to a region of the mutant DNA sequence set forth in FIG. 1 (or its corresponding RNA) containing one or more of the nucleotides at the corresponding 2328-, 2338-, 2772-, 2773- and/or 2784- position, other materials required to permit hybridisation. Such materials include appropriate buffers and washing solutions and a label and a substrate for the label if necessary. Normally the oligonucleotide would be labelled. If PCR is used to amplify nucleic acid prior to hybridisation then additional materials such as appropriate oligonucleotide primers which will amplify a region of the wild-type DNA sequence (or its corresponding RNA) or a region of the mutant DNA sequence set forth in FIG. 1 (or its corresponding RNA) containing one or more of the nucleotides at the 2328-, 2338-, 2772-, 2773- or 2784- position, appropriate enzymes and dNTP's (deoxy nucleotide triphosphates) should be included.

In one alternate format of the assay, the dNTP's in the amplification may or may not be coupled to a detector molecule such as a radiosotope, biotin, fluorochrome or enzyme.

It is also possible to detect zidovudine resistant mutations in the HIV-1 RT RNA isolated from clinical samples using an RNA amplification system. Using the methodology described by Guatelli et al. (Proc. Natl. Acad. Sci, (USA), 8/7, 1874–1878, (March 1990)) a target nucleic acid sequence can be replicated (amplified) exponentially in vitro under isothermal conditions by using three enzymatic activities essential to retroviral replication: reverse transcriptase, RNase H and a DNA-dependent RNA polymerase. Such a methodology may be employed followed by an hybridisation step to distinguish mutant from wild-type nucleotides as discussed previously.

The following examples are for illustration only and are not intended to limit the invention in any way. In the accompanying drawings.

Figure 4A:
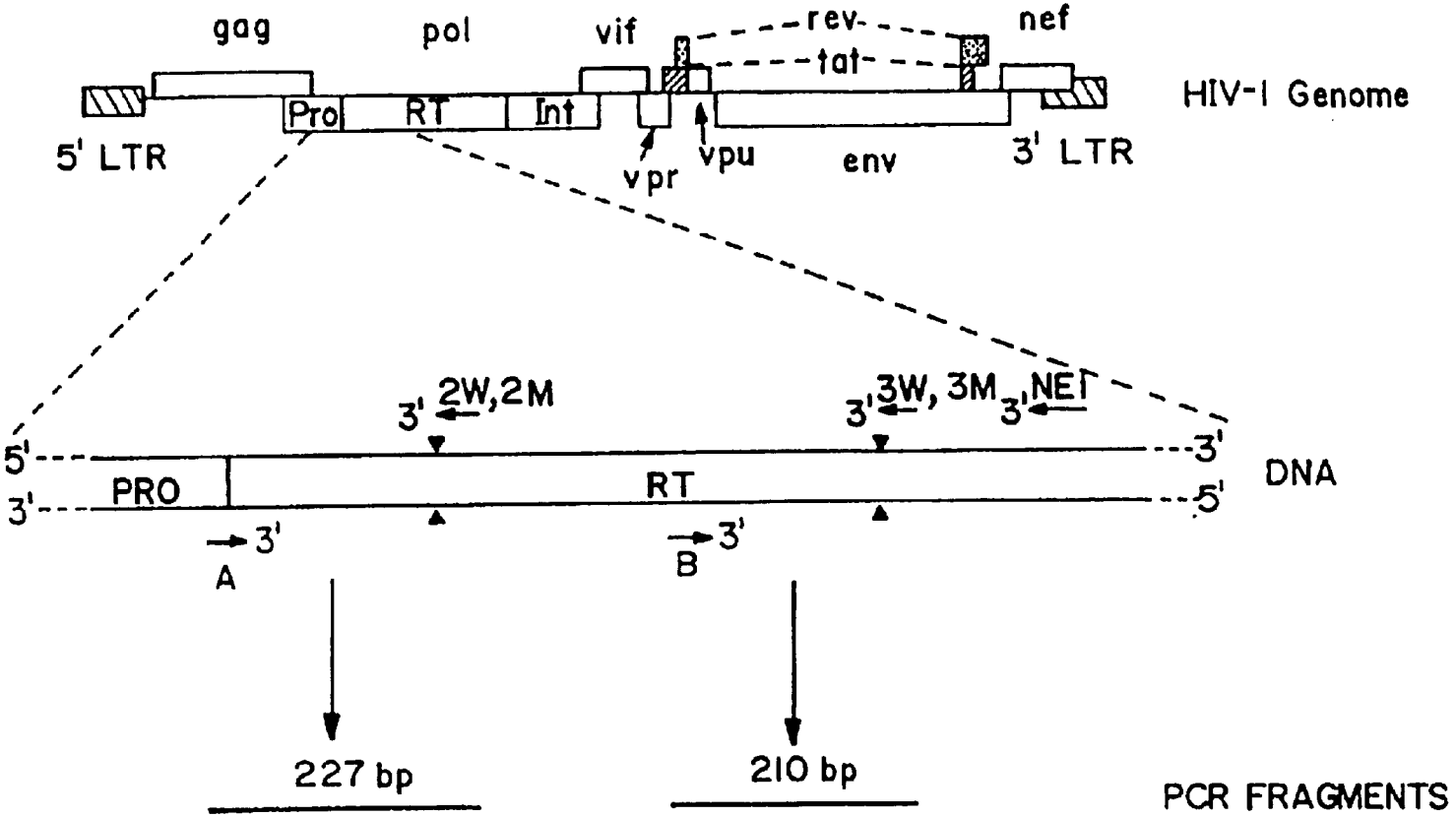
Figure 4C:
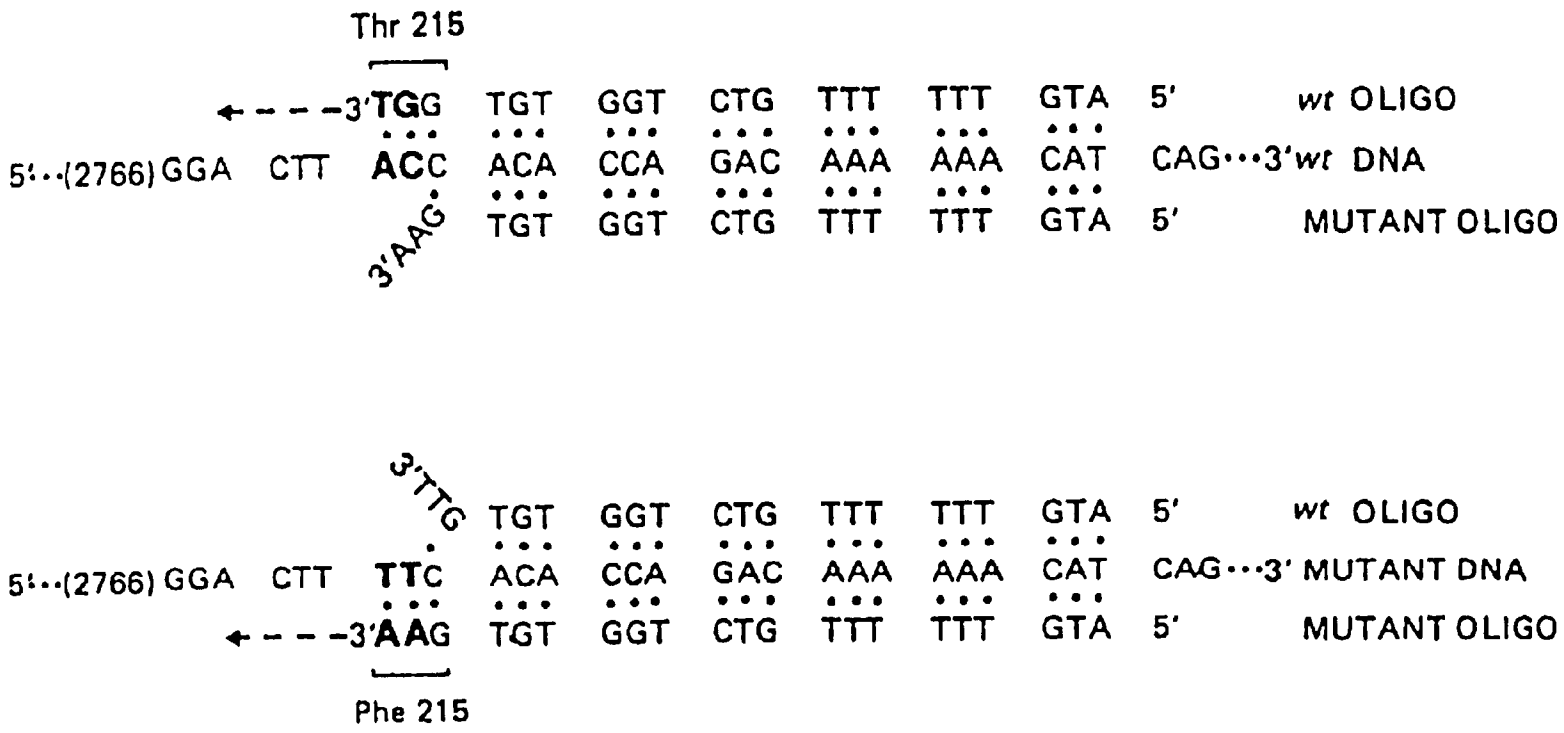

FIG. 4 shows mutational analysis of HIV RT using the polymerase reaction in which a. shows a schematic representation of the HIV-1 genone showing the location and orientation of oligonucleotide primers in the RT coding region used in PCR reactions. Primers 2W and 2M anneal to the sequence at codon 70 (indicated as ɪ) and are used separately with primer A to generate a DNA fragment of 227 bp. Primers 3W and 3M anneal to sequence at codon 215 (indicated as ɪ) and are used separately with primer B to generate a 210 bp fragment); b. shows details of PCR primers 2W and 2 M initiating DNA synthesis at codon 70. The sequence of each primer is shown with variation at the 3' end highlighted in bold letters where a correct match forms with target HIV DNA. In this situation Taq DNA polymerase can initiate DNA synthesis from the 3' end of the primer ←). Nucleotide sequence numbers according to Ratner at el., supra are shown in parenthesis. c. shows PCR primers 3W and 3M initiating DNA synthesis at codon 215. Sequence variation at the 3' end is highlighted in bold letters where a correct match is formed with target HIV DNA.

Figure 5:
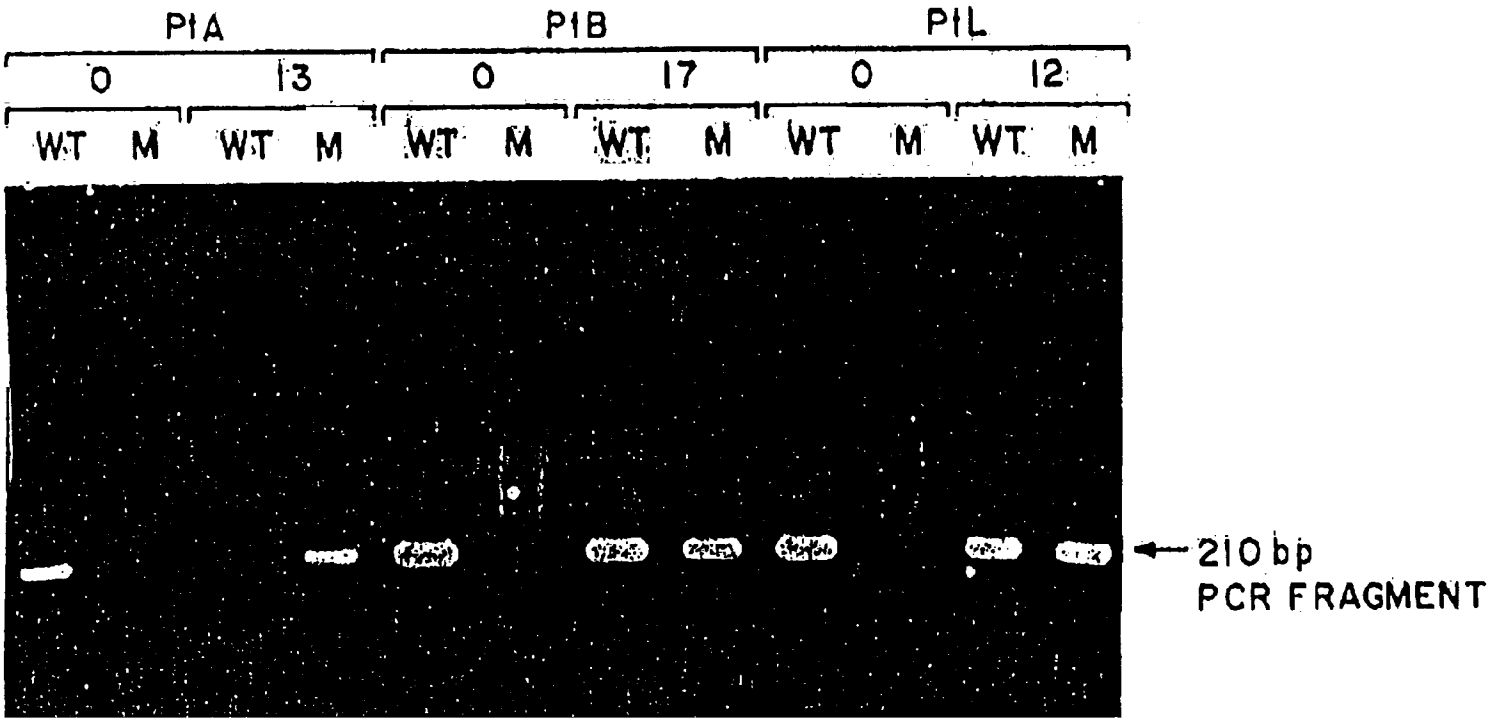

FIG. 5 shows a direct analysis of RT codon 215 in DNA from non-cultured PBL samples. Early and late PBL samples obtained from three patients with AIDS (ptA, ptB and ptL) receiving zidovudine therapy were subjected to "double" PCR to discriminate between wild type and mutant residues. Oligonucleotide primers A and NE1 were used in the initial PCR, producing a 768 bp fragment (see FIG. 4) and material from this amplification was used in the second PCR where primer B was paired separately With primer 3W (WT) or 3M (M) to discriminate between wild type and mutant nucleotides at condon 215. Produces (15 μl) from the second PCR were separated on a 1.5% agarose gel and stained with ethidium bromide. The numbers above pairs of lanes on the gel refer to the treatment time which each sample was obtained (in months). All patients received 1200 mg of zidovudine per day throughout the treatment period.

EXAMPLE 1

Isolation of HIV1 DNA

The isolation of HIV-1 was achieved according to methodology reported by Larder et al. PBL samples were prepared by separation on "Ficoll-hypaque" gradients and co-cultivated directly with MT-2 cells (approximately $10^6$ of each) after pre-stimulation for 24 to 72 hours with phytohaemag-glutinin (3 μg/ml). In many cases PBLs were cultured after long-term frozen storage. Cultures were maintained in RPMI 1640 supplemented with 10% fetal bovine serum, antibiotics, 2% interleukin-2, and polybrene (2 μg/ml) and expanded by addition of fresh MT-2 cells when a cytopathic effect was observed (between 4 and 14 days). HIV replication was confirmed by the detection of p24 antigen in culture supernatants (p24 antigen detection kit, Abbott, Chicago, Ill.). Virus were prepared from infected cultures and stored in aliquots at −70° C. All drug sensitivities were determined with virus pools that had been passaged no more than twice from original cultures. (Larder, B. A., Darby, G., Richman, D., Science, 243, 1731, (1989)).

DNA was extracted from MT-2 cells infected with HIV isolates as follows: $2\times10^6$ MT-2 cells were infected with HIV-1 at a multiplicity of approx. 0.1 $TCID_{50}$/cell and incubated at 37° C. for 3–4 days in RPM1 - 1640 medium supplemented with 10% foetal calf serum, polybrene (2 μg/ml) and antibiotics (sRPMI/10). The reference to Science, 246, 1155–1158 (1989) is made to permit the reader to obtain more information about Multiple Mutations in HIV-1 Reverse Transcriptase. The methodology for the extraction of DNA as provided in this Example is complete (Larder, B. A., Kemp, S. D., Science, 246, 1155–1158, (1989)).

DNA was extracted from the cell pellet by lysis in 0.4% SDS, 25 mM Tris-HCl, pHS, 25 mM, EDTA, and 150 mM NaCl and followed by Proteinase K (1 mg/ml) digestion for 1 hr at 50° C. Nucleic acid was recovered by phenol/chloroform extraction and ethanol precipitation, was treated with RNase A (10 μg/ml) and DNA was subjected to further phenol/chloroform extraction before ethanol precipitation.

EXAMPLE 2

Amplification and Cloning of HIV Reverse Transcriptase

The complete RT coding region (1.7 kb) was obtained for each HIV-1 isolate using polymerase chain reaction (PCR) amplification of infected cell DNA.

PCR is a powerful technique for selectively amplifying DNA or RNA sequences. It is an in vitro method for producing large amounts of a specific DNA fragment of defined length and sequence from small amounts of a template. PCR is based on the enzymatic amplification of a DNA fragment that is flanked by two oligonucleotide primers that hybridise to opposite strands of the target sequence. The primers are oriented with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other primer, each cycle essentially doubles the amount of the DNA fragment produced in the previous cycle. This results in the exponential accumulation of the specific target fragment, up to several millionfold in a few hours. The method can be used with a complex template such as genomic DNA and can amplify a single-copy gene contained therein. It is also capable of amplifying a single molecule of target in a complex mixture of RNAs or DNAs and can, under some conditions, produce fragments up to ten kilobase pairs long. (White, T. J., Arnheim, N., and E. Hich, A., Technical Focus Vol. 5, No. 6, p185 June 1989).

Figure 3:
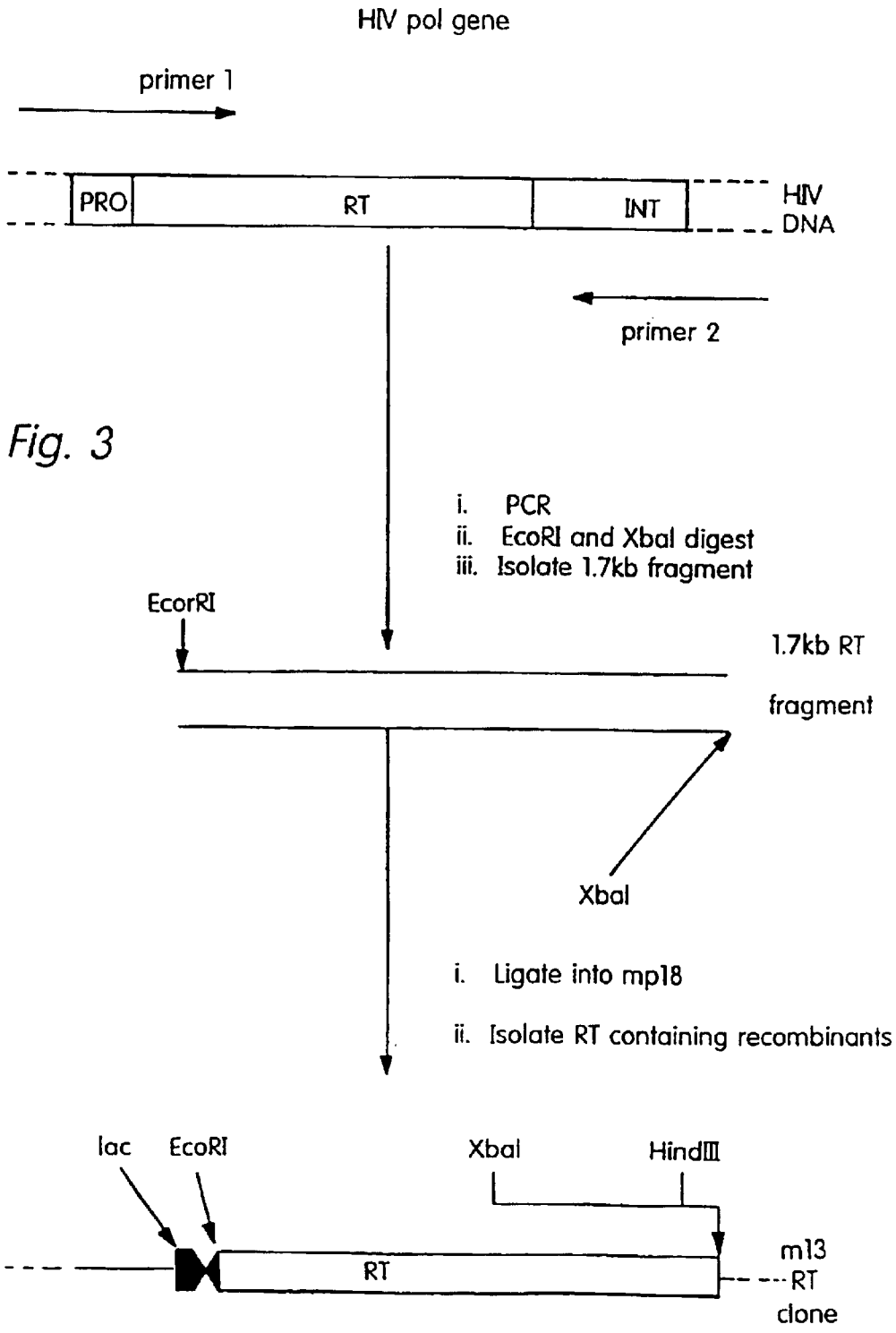
FIG. 3 shows the scheme used to amplify and clone HIV RT.

A diagramatic representation of the scheme used to amplify and clone HIV RT is shown in FIG. 3. Total DNA was extracted from cells infected with HIV isolates and the entire 1.7 kb fragment of the RT coding region was obtained by PCR (Saiki, R. K., et al. Science 239, 487 (1988)) HIV-1 DNA was obtained as in Example 1. Approximately 1 μg of this DNA was used per PCR reaction to amplify the complete RT coding region. Each reaction mix (100 μl) contained 25 mM KCl, 1.5 mM $MgCl_2$, 50 mM tris-HCl, pH8.3, 0.1 mg/ml bovine serum albumin, 0.2 mM each of dATP, dGTP, dCTP, TTP, 0.25 μg each primer and 2.5 units of Taq DNA Polymerase (Perkin-Elmer Cetus). These mixtures were heated at 100° C. for 2 mins prior to addition of Taq DNA polymerase, overlaid with 100 μl light mineral oil and subjected to 30 cycles consisting of a denaturation step (1 min 30 secs, 94° C.) primer annealing (2 min, 37° C.) and DNA synthesis (10 min, 72° C.) using a Perkin-Elmer Cetus DNA thermal cycler. The oligonucleotide primers, made using an Applied Biosystems 381A synthesiser, were as follows: at the 5' end of RT, 5'-TTGGACTTTGAATTCTCCCATTAG-3' and 5'-TGTACTTTGAATTCCCCCATTAG-3' (two primers were used to accommodate sequence variation seen in this region) and at the 3' end, 5'-CTTATCTATTCCATCTAGAAATAGT-3'.

HIV RT obtained by PCR amplification was digested with EcoRI and XbaI, whose recognition sites were built into the 5' and 3" ends by the PCR primers, fragments were purified from agarose gels and ligated with the replicative form (RF) of M13mp18, previously digested with EcoRI and XbaI. HIV RT (1.7Kb) obtained by PCR amplification (Saiki, R. K., et al. Science 239, 487 (1988)) was digested with EcoRI and XbaI (BRL), purified from agarose gels and ligated with the M13 vector mp18 pre-digested with EcoRI and XbaI (see FIG. 3). The ligation mixture was used to transform E. coli (strain TG-1) made competent as described (D. Hanahan, J. Mol. Biol. 166, 557 (1983)). Single-stranded DNA was prepared from these constructs for nucleotide sequencing. Clones able to express functional RT enzyme were sequenced using the well-known dideoxynucleotide chain-termination method (Sanger, F., Nicklen, S., Coulson, A. R., Proc. Natl. Acad. Sci., USA, 74, 5463, (1977)). Table 1 shows details of the RT clones obtained by this procedure and lists the HIV isolates from which they were derived. The complete sequence of 6 RT clones was obtained (sensitive and resistant isolate pairs the three individuals) and partial sequence data were obtained from additional isolates.

PCR primers can be designed to incorporate a restriction enzyme recognition site such as EcoRI at the 5' end of the HIV-1 RT gene and a restriction enzyme such as Xbal at the 3' end. Digestion of each fragment with restriction enzymes allows subsequent cloning into a suitable vector such as an M13 mp18 based vector.

EXAMPLE 3

Properties of HIV-1 Isolates and M13 RT Clones Derived from Them. Mutations in HIV-1 RT conferring zidovudine Resistance HIV isolates derived from untreated and treated individuals are shown in Table 1 with duration of therapy at the time they were obtained and the zidovudine sensitivity. Where multiple isolates were obtained from the same individual, isolates are lettered in temporal order. Fifty per cent inhibitory dose ($ID_{50}$) values were obtained by plaque-reduction assay with HT4-6C cell monolayers Inhibition of plaque formation (foci of multinucleated giant cells) was determined by infecting monolayers of HeLa HT4-6C cells with cell-free HIV preparations. The input inoculum was adjusted to give 100 to 300 plaques per well (in 24-well plates) in the no-drug control cultures. Virus was allowed to absorb for one hour at 37° C. prior to the addition of inhibitor in the culture medium (Dulbecco's modification of Eagle's medium, containing 5% fetal bovine serum plus antibiotics). After 3 days of incubation, monolayers were fixed with 10% formaldehyde and stained with 0.25% crystal violet to visualize plaques. This staining procedure revealed obvious individual dense foci of multinucleated giant cells. $ID_{50}$ values were derived directly from plots of 50% plaque reduction cersus inhibitor concentration. (Larder, B. A. Darby. G., Richman, D. D., Science, 243, 1731, (1989); Chesebro, B. D., Wehrly, K., J. Virol., 62, 3779 (1988).).

The amino acid residue at four positions in HIV-1 RT important for zidovudine resistance are illustrated for HIV isolates. Wild-type residues at the positions of interest are as follows: Asp 67, Lys 70, Thr 215 and Lys 219.

Figure 2:
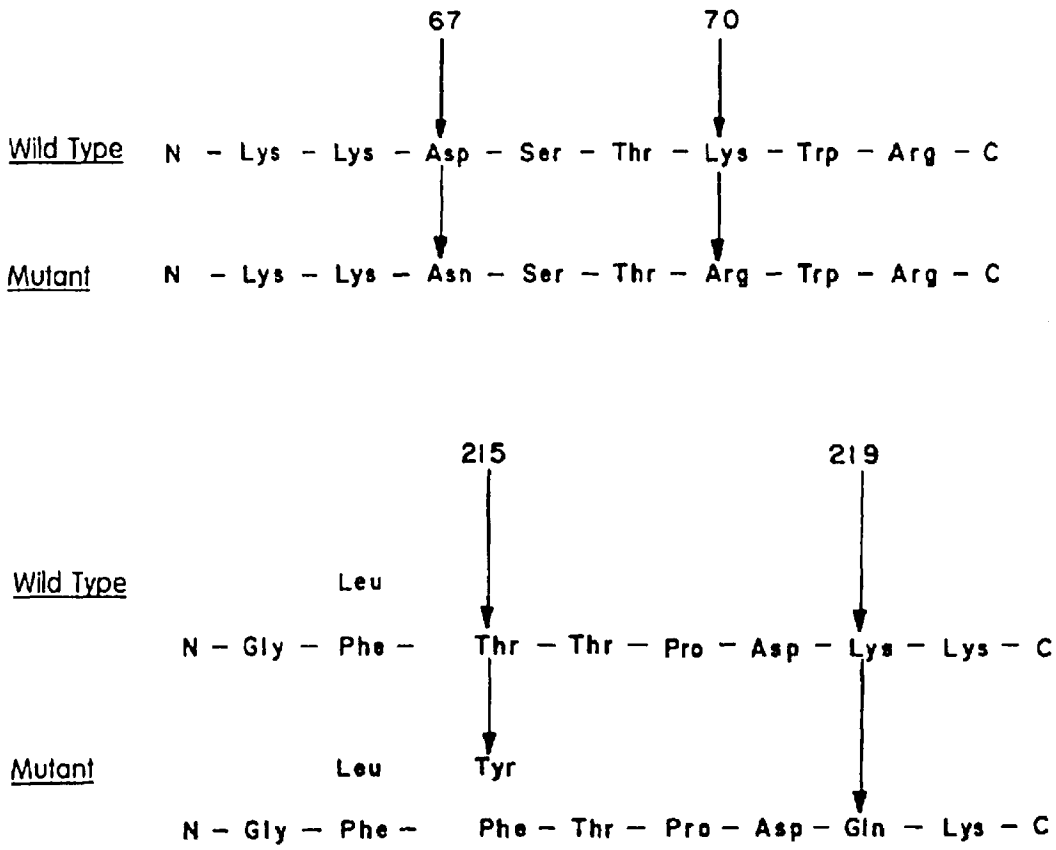
FIG. 2 shows the amino acid changes at the four positions in HIV-1 RT that confer resistance to zidovudine.

Comparison of predicted complete amino acid RT sequences from sensitive and highly-resistant isolate pairs obtained from the same individuals (patients A012, AO18 and P022) revealed substantial differences of between 14–17 residues. In each case however, we identified amino acid changes at four residues (Asp 67→Asn, Lys 70→Arg, Thr 215→Phe or Tyr, and Lys 210→Gln) in the highly resistant isolates not seen in the sensitive counterparts (FIG. 2). Analysis of sensitive and highly-resistant isolate pairs from a further two individuals (patients A036 and PO26) revealed the same mutations at positions 67, 70 and 215, whilst retaining the wild-type Lys at residue 219 (FIG. 2). In cases where multiple M13 clones were sequenced from an isolate only minor sequence variation was seen. It was interesting that published HIV-1 RT sequences showed absolute conservation of all four residues in every strain (G. Myers et al., (eds) Human retroviruses and AIDS: a compilation and analysis of nucleic acid and amino acid sequences (Theoretical Biology and Biophysics, Los Alomos, N.M.) II-22 (1989), strongly implicating these mutations in zidovudine-resistance.

TABLE 1

| HIV ISOLATE | DURATION OF THERAPY (Months) | ZIDOVUDINE SENSITIVITY ($ID_{50}$ μM) | RT ACTIVITY M13 CLONE (% Control) | AMINO ACID RESIDUES IN RT 67 | 70 | 215 | 219 |
|---|---|---|---|---|---|---|---|
| A012B | 1 | 0.01 | 20 | Asp | Lys | Thr | Lys |
| A012D | 26 | 2 | 85 | Asn | Arg | Phe | Gln |
| A018A | 0 | 0.01 | 62 | Asp | Lys | Thr | Lys |
| A018C | 14 | 2.3 | 79 | Asn | Arg | Tyr | Gln |
| A036B | 2 | 0.01 | 47 | Asp | Lys | Thr | Lys |
| A036C | 11 | 0.6 | 52 | Asp | Lys | Tyr | Lys |
| A036D | 20 | 5.6 | 46 | Asn | Arg | Tyr | Lys |
| P022A | 1 | 0.01 | 20 | Asp | Lys | Thr | Lys |
| P022C | 16 | 1.4 | 67 | Asn | Arg | Phe | Gln |
| P026A | 0 | 0.01 | 76 | Asp | Lys | Thr | Lys |
| P026B | 11 | 2.8 | 78 | Asn | Arg | Tyr | Lys |
| P035A | 6 | 0.56 | 55 | Asp | Lys | Tyr | Lys |

EXAMPLE 6

Zidovudine-sensitivity of HIV Valiant Created by Site-Directed Mutagensis

To text whether multiple mutations in the RT gene could account for high level resistance, an infectious molecular clone of HIV containing only the four mutations described above was constructed (the isolate AO12D) to assess the sensitivity of virus produced from this clone by transfection of T-cells. A 2.55 kb fragment of the HIV Pol gene from infectious clone HXB2-D (Fisher, A. G., et al., Nature 316, 262, 1985) inserted into the M13 vector mp19, was used as a target for site-directed mutagenesis (Larder, B. A., Kemp, S. D., Purifoy, D. J. M., Proc. Natl. Acad. Sci., USA, vol 86; p.4803 (1989)

Specific nucleotide changes were simultaneously introduced into the RT gent using two synthetic oligonucleotides and mutations were confirmed by nucleotide sequencing (Sanger, F., Nicklen, S. A., Coulson, A. R., Proc. Natl. Acad. Sci., USA. 74, 5463, (1977)). To reconstruct the full-length clone, a 1.9 kb BalI restriction fragment containing the mutations in RT was removed from the pol gene M13 clone and transferred into HXB2-D (Larder, B. A., Kemp, S. D., Purifoy, D. J. M., Proc. Natl. Acad. Sci, USA, Vol. 86, p4803, (1989)). DNA prepared from wild-type and mutant infectious clones was then used to transfect the T-cell lymphoblastoid line, MT-4 (Harada, S., Koyanagi, U., Yamomoto, N., Science, 229, 563, (1985)), by electroporation. Virus-induced CPE was observed in each culture at similar times (after 2–4 days) and virus stocks were prepared 6–7 days post transfection. Wild type and mutant HIV isolates (HXB2-D and HIVRTMC respectively) were titrated by plaque assay in the HeLa-CD4$^+$ cell line, HT4-6C, and then tested for sensitivity to zidovudine by plaque-reduction assay in HT4-6C cells (Larder, B. A., Darby, G., Richman, D. D., Science, 243, 1731, (1989); Chesebro. B. D., Wehrly, K., J. Virol., 62 3779, (1988)). The results of these experiments as shown in Table 2 clearly demonstrate that the mutant virus constructed by site-directed mutagenesis was highly resistant to zidovudine. The $ID_{50}$ value for HIVRTMC increased about 100-fold compared to wild-type virus and the magnitude of resistance was similar to that of naturally occurring HIV isolates containing similar mutations in the RT gene (Table 2).

TABLE 2

| HIV ISOLATE | ZIDOVUDINE SENSITIVITY (Mean $ID_{50}$, μM) | FOLD INCREASE |
|---|---|---|
| HXB2.D | 0.013 (0.005) | 1 |
| HIVRTMC | 1.28 (0.24) | 98 |
| A012B | 0.013 (0.005) | 1 |
| A012D | 2.56 (1.03) | 197 |

EXAMPLE 5

Selective amplification of HIV DNA to detect resistance mutations

DNA for PCR was obtained from MT-2 cells ($2\times10^6$) infected with HIV isolates at a multiplicity of 0.1 $TCID_{50}$/ml (fifty per cent tissue culture infectious dose per ml, as determined by terminal dilution of virus stocks in MT-2 cells) and incubated at 37° C. for 3–4 days in RPMI 1640 medium supplemented with 10% fetal bovine serum, polybrene (2 μg/ml) and antibiotics. DNA was extracted from cell pellets by lysis in 0.4% SDS, 25 mM Tris HCl, pHS, 25 mM EDTA and 150 mM NaCl. After digestion with proteinase K (1 mg/ml, 1 h at 50° C.) DNA was recovered by phenol extraction and ethanol precipitation. Approximately 1 μg of this material was used per PCR reaction (100 μl) which contained: 25 mM KCl, 50 mM Tris HCl, pH8.3, 0.1 mg/ml bovine serum albumin (BSA), 0.2 mM each of dATP, dGTP, dCTP and dTTP, 0.25 μg of each oligonucleotide primer with the following concentrations of $MgCl_2$ for specific combinations of primer pairs:

Primer A with 1W and 1M (to analyse codon 67): 2 mM $MgCl_2$

Primer A with 2W and 2M (to analyse codon 70): 5 mM $MgCl_2$

Primer B with 3W and 3M (to analyse codon 215): 1.8 mM $MgCl_2$

Primer B with 4W and 4M (to analyse codon 219): 1.5 mM $MgCl_2$

Reaction mixtures were heated at 100° C. for 2 mins prior to addition of Taq DNA polymerase (2.5 units, Perkin-Elmer Cetus), overlaid with 100 μl light mineral oil and subjected to 30 cycles consisting of a denaturation step (1 min, 94° C.), primer annealing (30 sec, 40° C. for reactions to analyse codon 70 (primer A with 2W and 2M) and codon 219 (primer B with 4W and 4M) or 45° C. for reactions to analyse codon 67 (primer A with 1W and 1M) and codon 215 (primer B with 3W and 3M) and DNA synthesis (30 sec, 72° C.) using a Perkin-Elmer Cetus DNA thermal cycler. The oligonucleotide primers (FIG. 4) were synthesised using an Applied Biosystems 381A machine. 10 μl of each reaction mixture was run on 1.5% TBE agarose gels and DNA was visualized by ethidium bromide staining. The sequence of PCR primers 2W, 2M, 3W and 3M are shown in FIG. 4b and c. The sequences of the other oligonucleotide primers were as follows:

```
primer A,      5'-TTCCCATTAGTCCTATT-3';
primer B,      5'-GGATGGAAAGGATCACC-3';
primer IW,     5'-TTTTCTCCATTTAGTACTGAC-3';
primer IM,     5'-TTTTCTCCATCTAGTACTGAT-3';
primer 4W,     5'-AGGTTCTTTCTGATGTTTTAT-3';
primer 4M,     5'-AGGTTCTTTCTGATGTTTTAG-3'.
```

EXAMPLE 6

Construction of HIV variants with defined Combinations of mutations in RT

Variants were constructed to mimic mutants identified by DNA sequence analysis of clinical isolates and in addition, a number of mutants were made containing combinations of changes in RT not yet seen. The nucleotide sequence of RT derived from the proviral clone HXB2-D (Fisher, A. G., Collatti, E., Ratner, L. Gallo, R. C. and Wong Staal, F., Nature (London), 316, 262–265, (1985)) was initially altered by site directed mutagenesis. A pol gene DNA fragment from M13 clones containing altered RT was mixed with HXB2-D that had a Bali restriction enzyme fragment encompassing the RT region removed. These mixtures were used to co-transfect MT-2 cells by electroporation in order to allow formation of infectious virus variants through homologous recombination. Mutations in RT were created by site-directed mutagenesis of the previously described M13 clone mpRT1/H, which contains a 2.55 kb Bgl II to EcoRI fragment of the wild type HIV pol gene (Larder, B. A., Kemp, S. D., and Purifoy, D. J. M., Proc. Natl. Acad. Sci., (USA), 86, 4803–4807 (1989)). All mutants were verified by nucleotide sequence analysis (Sanger, F., Nicklen, S, and Coulson, A. R. Proc. Natl. Acad. Sci., USA, 74, 5463–5467 (1977)). Wild type virus HXB2 and mutants were derived by homologous recombination in MT-2 cells (Clavel, F., Hogan, M. D., Willey, R. L., Strebel, K., Martin, M. A. and Repaske, R., J. Virol., 63, 1455–1459 (1989); Srinivasan, A., et al., Proc. Natl. Acad. Sci., (USA) 86, 6388–6392 (1989)) by co-transfecting a wild type full length HIV clone missing most of RT and the pol gene fragment from mpRT1/H M13 clones. Wild type infectious clone HXB2-D (Fisher, A. G., Collati, E., Rather, L., Gallo, R. C., and Wong-Staal, F., Nature (London), 316, 262–265, (1985)) was digested with Msc I (Bal I), releasing a 1.9 kb fragment comprising the majority of RT (Ratnet, L. et al., Nature (London) 313, 277–284, (1985)) and the large fragment was purified from agarose gels. The replicative form (double stranded DNA) of mpRT1/H or mutated clones were digested with EcoRI and Hind III to linearize the pol gene fragment and 5 μg of each was mixed with 5 μg of gel purified HXB2-D DNA (with the Msc I fragment removed). Each mixture was used to transfect MT-2 cells by electroporation as described (Larder, B. A., Kemp, S. D. supra.) and infectious virus (recovered in culture supernatants at around 14 days post transfection) was stored in aliquots at −70° C. The genotype of mutant viruses were verified by DNA sequence analysis of RT cloned from these isolates by PCR.

Virus isolates recovered from these cultures were tested for sensitivity to zidovudine by plaque reduction assay in HT4-6C cells. Virus variants were generally more resistant with increasing numbers of mutations (table 4), which was in broad agreement with DNA sequence data obtained from clinical isolates (table 3). For example, recombinants RTMF (Thr215→Tyr) and RTMC/WT (Asp6-7→Asn, Lys70→Arg) were less resistant to zidovudine than variant RTMC/F (Asp67→Asn, Lys70→Arg, Thr215→Tyr) and the degree of resistance of RTMC/F was about equal to the sum of $ID_{50}$ values seen with RTMF and RTMC/WT.

TABLE 3

| HIV Isolate | Months of Therapy | Zidovudine Sensitivity ($ID_{50}$ μM) | RT sequence | PCR Analysis Codon 70 WT | PCR Analysis Codon 70 M | PCR Analysis Codon 215 WT | PCR Analysis Codon 215 M |
|---|---|---|---|---|---|---|---|
| A001A | 0 | 0.03 | . . . . | + | − | + | − |
| A001B | 12 | 0.11 | ( . $R_{70}$ . . / $N_{67}$ $R_{70}$ . $Q_{219}$ | − | + | + | − |
| A012B | 2 | 0.01 | . . . . | + | − | + | − |
| A012D | 26 | 2 | $N_{67}$ $R_{70}$ $F_{215}$ $Q_{219}$ | − | + | − | + |
| A018A | 0 | 0.01 | . . . . | + | − | + | − |
| A018C | 14 | 4 | $N_{67}$ $R_{70}$ $Y_{215}$ $Q_{219}$ | − | + | − | + |
| A036B | 2 | 0.01 | . . . . | + | − | + | − |
| A036C | 11 | 0.67 | . . $Y_{215}$ . | + | + | − | + |
| A036D | 20 | 5.6 | $N_{67}$ $R_{70}$ $Y_{215}$ . | − | + | − | + |
| A025A | 24 | 0.11 | . $R_{70}$ . . | − | + | + | − |
| P035A | 6 | 0.18 | . . $Y_{215}$ . | + | − | − | + |
| P036A | 6 | 0.35 | $N_{67}$ $R_{70}$ $Y_{215}$ . | − | + | − | + |

Properties of HIV isolates obtained before and during zidovudine therapy Table 4

| HIV Variant | RT Sequence | | | | Zidovudine sensitivity ($ID_{50}$, μM) | Fold Increase |
|---|---|---|---|---|---|---|
| HXB2 | . | . | . | . | 0.01 | 1 |
| HIVRTMI | $N_{67}$ | . | . | . | 0.01 | 1 |
| HIVRTMJ | . | $R_{70}$ | . | . | 0.08 | 8 |
| HIVRTMF | . | . | $Y_{215}$ | . | 0.16 | 16 |
| HIVRTMK | . | . | $S_{215}$ | . | 0.01 | 1 |
| HIVRTMA2 | . | . | . | $Q_{219}$ | 0.01 | 1 |
| HIVRTMC/WT | $N_{67}$ | $R_{70}$ | . | . | 0.17 | 17 |
| HIVRTMA3 | . | . | $F_{215}$ | $Q_{219}$ | 0.22 | 22 |
| HIVRTMC/A2 | $N_{67}$ | $R_{70}$ | . | $Q_{219}$ | 0.28 | 28 |
| HIVRTMC/F | $N_{67}$ | $R_{70}$ | $Y_{215}$ | . | 0.35 | 35 |
| HIVRTMC | $N_{67}$ | $R_{70}$ | $F_{215}$ | $Q_{219}$ | 1.66 | 166 |

Zidovudine sensitivity of HIV variants with defined mutations in reverse transcriptase

EXAMPLE 7

Detection of mutations in DNA from non-cultured lymphold cells

The above PCR assay (Example 5) was adapted to enable direct detection of mutations associated with zidovudine resistance in DNA from PBL samples from infected individuals that had not been cultured to obtain virus. As this material generally contains considerably less HIV DNA than that in infected lymphoid cell cultures, we used a "double PCR" (or nested set) protocol (Simmonds, P., et al., Supra.) to boost the amount of target HIV RT DNA signal in the samples. Therefore, we initially amplified a 768b fragment from within the RT region which encompassed all the commonly observed mutations (PCR primers A and NE1 were used in this amplification, see FIG. 4a). A small amount of this pre-amplified material was then used in the second PCR with primer pairs designed to allow discrimination of wild type and mutant residues. Results of a typical analysis of amino acid residue 215 are shown in FIG. 5. PBL samples were obtained from three individuals with AIDS prior to initiation of zidovudine therapy and after 12–17 months of therapy. The pre-treatment samples all appeared to be wild type, whilst the post-treatment initiation samples were either mutant or appeared a mixture of both (FIG. 5).

Detection by PCR of mutations in DNA from non-cultured PBL samples

DNA was extracted from about $2\times10^6$ PBLs as described above for MT-2 cell cultures. 0.5–1 μg of this material was used in the initial PCR (100 μl) which contained 25 mM KCl, 1.8 mM $MgCl_2$, 50 mM Tris HCl, pH 8.3, 0.1 mg/ml BSA, 0.2 mM each of dATP, dGTP, dCTP and dTTP plus 0.25 μg of each primer (primer A and primer NE1). Reaction mixtures were processed as described in Example 5, and subjected to 30 cycles of 1 min 94° C., 1 min 45° C. and 2 min 72° C. Following amplification, samples were extracted by the addition of 100 μl chloroform and 0.5 μl of each was added directly to reaction tubes containing all constituents of the relevant PCR mixture. Samples were overlaid with 100 μl light mineral oil and heated to 94° C. for 5 mins prior to thermal cycling. Reaction mixtures and thermal cycle times for this second round of PCR were exactly as described above for selective amplification (Example 5) to detect specific mutations (i.e. primer A was paired with 2W or 2M, or primer B was paired with 3W or 3M). Inclusion of 1 μg herring sperm DNA in each reaction was round to enhance the selectivity of the second PCR. In addition, due to the extreme sensitivity of "double" PCR, stringent precautions were taken to avoid cross-contamination of samples and PCR reagents. Control reactions were always performed with no added DNA to ensure no spurious amplification had occurred. The sequence of PCR primer NE1 was as follows: 5'-TCATTGACAGTGCAGCT-3' This primer anneals downstream of primers 3W and 3M as shown in FIG. 4a.

Figure 1:
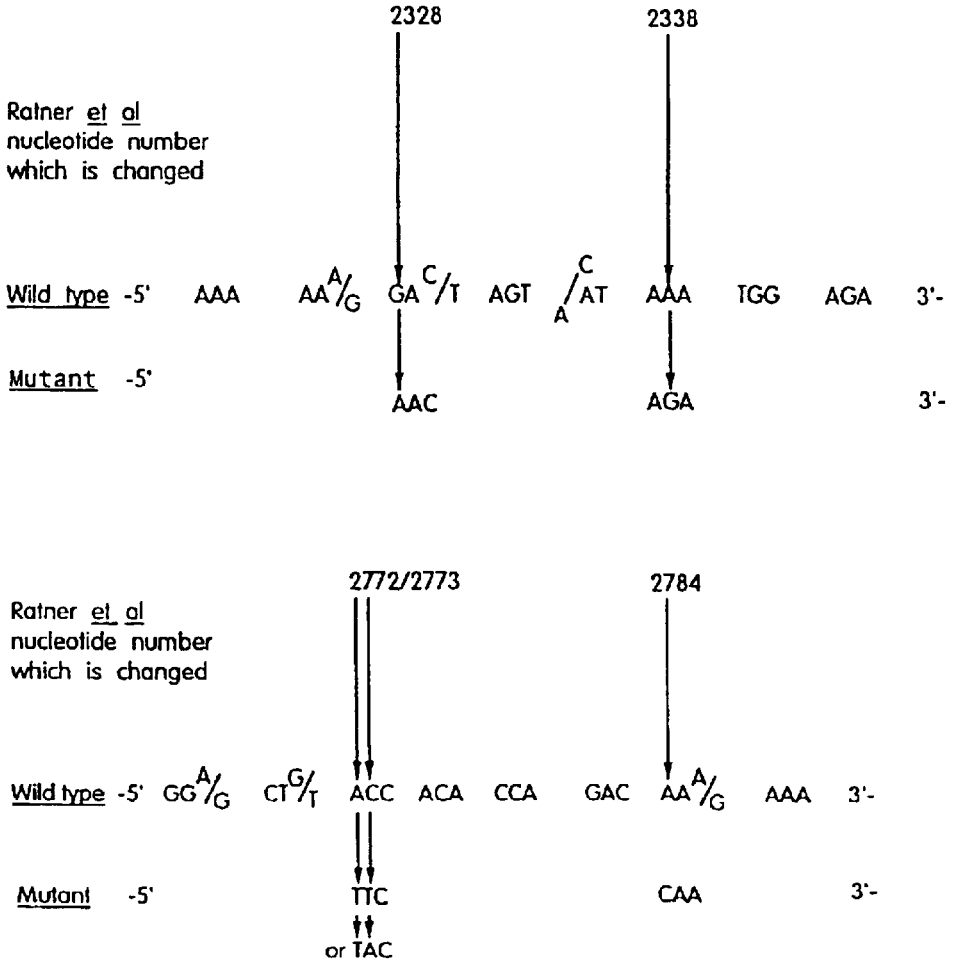
FIG. 1 shows the nucleotide changes at the five positions in HIV-1 RT that confer resistance to zidovudine. Numbering of the nucleotides is as reported by Rather et al., Nature, 313, 277, (1985).

We claim:

[1. A method for determining the sensitivity of an HIV-1 samples to zidovudine, which comprises:

(a) isolating HIV-1 DNA extracted from human cells or HIV-1 RNA isolated from body fluids, (b) hybridizing a detectably labeled oligonucleotide to the HIV-1 DNA isolated in step (a), the oligonucleotide having at its 3' end at least 15 nucleotides complementary to a region of the weld type DNA sequence, its corresponding RNA, to a region of the mutant DNA sequence set forth in FIG. 1, or its corresponding RNA, wherein the oligonucleotide terminates of the 3'-end with said at least 15 nucleotides at the 2328, 2338, 2772, 2773, or 2784 position, (c) attempting to extend the oligonucleotide at its 3'-end, (d) ascertaining the presence or absence of a detectably labeled extended oligonucleotide, (d) correlating the presence or absence of a detectably labeled extended oligonucleotide in step (d) with the sensitivity of the HIV-1 samples to zidovudine.]

[2. A method for determining the sensitivity of an HIV-1 sample to zidovudine which comprises:

(a) isolating nucleic acid from the sample, (b) hybridizing a detectably labeled oligonucleotide to the HIV-1 nucleic acid isolated in step (a), the oligonucleotide having at least 15 nucleotides complementary to a region of the wild type DNA sequence, its corresponding RNA, to a region of the mutant DNA sequence set forth in FIG. 1, or its corresponding RNA, wherein said oligonucleotide having at least 15 nucleotides contains at least one nucleotide at the 2328, 2338, 2772, 2773, or 2784 position, (c) ascertaining whether or not any of the resulting hybrids of the detectably labeled oligonucleotide and nucleic acid have complementary nucleotides at one of these positions, and (d) correlating the presence of absence of a detectably labeled nucleic acid hybridization product formed instep (b) with the sensitivity of an HIV-1 sample to zidovudine.]

[3. In the method of claim 1 or 2, prior to step (b), the isolated nucleic acid is amplified prior to hybridization.]

[4. A method as claimed in claim 1 or 2 wherein the detectable label on the oligonucleotide is an enzyme, radioisotope or fluorochrome.]

[5. A method for determining the sensitivity of a patient sample containing HIV-1 to zidovudine, comprising:

detecting a substitution at one or more of positions 2328, 2338, 2772, 2773and/or 2784 in the reverse transcriptase gene or HIV-1 from the patient sample relative to the wildtype sequence shown in FIG. 1, wherein the presence of one or more substitutions correlates with decreased sensitivity of the sample to zidovudine.]

[6. The method of claim 5, wherein the substitution is detected at position 2328.]

[7. The method of claim 5, wherein the substitution is detected at position 2338.]

[8. The method of claim 5, wherein the substitution is detected at position 2772.]

[9. The method of claim 5, wherein the substitution is detected at position 2773.]

[10. The method of claim 5, wherein the substitution is detected at position 2784.]

[11. The method of claim 5, further comprising:

assessing the sensitivity of the HIV sample to zidovudine from the presence or absence of a substitution at one or more of the nucleotides.]

[12. A method for determining the sensitivity of a patient sample containing HIV-1 to zidovudine, comprising:

hybridizing an oligonucleotide to a HIV-1 nucleic acid from the patient sample, wherein the oligonucleotide is complementary to a HIV-1 reverse transcriptase sequence or its complement including one or more nucleotides as positions 2328, 2338, 2772, 2773,and/or 2784;

detecting hybridization between the oligonucleotide and the nucleic acid to determine a nucleotide present at one or more of positions 2328, 2338, 2773and/or 2784, the identity of the nucleotide indicating whether the HIV sample is sensitive to zidovudine.]

[13. The method of claim 12, wherein the oligonucleotide is immobilized to a support.]

[14. The method of claim 13, wherein the HIV-1 nucleic acid is labelled and the oligonucleotide is unlabelled.]

[15. An oligonucleotide probe for determining a nucleotide at one or more of positions 2328, 2338, 2772, 2773and/or 2784 in a HIV-1 reverse transcriptase gene, wherein the probe is complementary to a HIV-1 reverse transcriptase sequence or its complement including at least one of the positions.]

[16. The oligonucleotide probe of claim 15 that hybridizes to the wildtype form of the reverse transcriptase gene shown in FIG. 1 or its complement.]

[17. The oligonucldotide probe of claim 15 that hybridizes to a mutant form of the reverse transcriptase gene shown in FIG. 1 or its complement.]

[18. The oligonucleotide probe of claim 15, wherein the probe includes position 2328of the HIV-1 reverse transcriptase sequence or its complement and hybridization of the probe to the sequence or its complement determines the nucleotide occupying position 2328.]

[19. The oligonucleotide probe of claim 15, wherein the probe includes position 2338of the HIV-1 reverse transcriptase sequence or its complement and hybridization of the probe to the sequence or its complement determines the nucleotide occupying position 2338.]

[20. The oligonucleotide probe of claim 15, wherein the probe includes position 2772 of the HIV-1 reverse transcriptase sequence or its complement and hybridization of the probe to the sequence or its complement determines the nucleotide occupying position 2772.]

[21. The oligonucleotide probe of claim 15, wherein the probe includes position 2773 of the HIV-1 reverse transcriptase sequence or its complement and hybridization of the probe to the sequence or its complement determines the nucleotide occupying position 2773.]

[22. The oligonucleotide probe of claim 15, wherein the probe includes position 2784 of the HIV-1 reverse transcriptase sequence or its complement and hybridization of the probe to the sequence or its complement determines the nucleotide occupying position 2784.]

[23. A method of screening a HIV patient being or to be treated with a drug, comprising:

obtaining a sample from the patient;

detecting one or more substitutions in a reverse transcriptase gene of a HIV genome from the patient sample; and correlating the one or more substitutions with decreased sensitivity to the drug.]

[24. The method of claim 23, further comprising:

diagnosing decreased sensitivity to the drug in a second patient infected with HIV having a reverse transcriptase gene with at least one of the substitutions.]

*25. A method for determining the sensitivity of a patient sample containing HIV-1 to zidovudine, comprising:*

*(a) isolating a nucleic acid sample from cells of the patient;*

*(b) amplifying a reverse-transcriptase sequence from the nucleic acid sample;*

*(c) performing dideoxy sequencing of the reverse-transcriptase sequence; and*

*(d) detecting a substitution at one or more of positions 2328, 2338, 2772, 2773 and 2784 in the reverse transcriptase sequence of HIV-1 from the patient sample relative to the wild type sequence shown in FIG. 1, wherein the presence of one or more substitutions correlates with decreased sensitivity of the sample to zidovudine.*

*26. The method of claim 25, wherein step (b) is performed by amplifying HIV-1 RNA by RT-PCR.*

*27. The method of claim 25, wherein step (b) is performed by amplifying HIV-1 DNA by PCR.*

*28. The method of claim 25, wherein the amplifying is performed through the use of nested primers.*

*29. The method of claim 25, wherein the patient has been treated with zidovudine prior to performing step (a).*

*30. The method of claim 25, wherein the patient has not been treated with zidovudine prior to performing step (a).*

*31. The method of claim 25, wherein the substitution is detected at position 2328.*

*32. The method of claim 25, wherein the substitution is detected at position 2338.*

*33. The method of claim 25, wherein the substitution is detected at position 2772.*

*34. The method of claim 25, wherein the substitution is detected at position 2773.*

*35. The method of claim 25, wherein the substitution is detected at position 2784.*

*36. A method for determining the sensitivity of a patient sample containing HIV-1 to zidovudine, comprising:*

*(a) hybridizing an immobilized oligonucleotide that is at least 15 nucleotides long to an HIV-1 nucleic acid from the patient sample, wherein the oligonucleotide is complementary to an HIV-1 reverse transcriptase sequence or its complement including one or more nucleotides at positions 2328, 2338, 2772, 2773, and/or 2754; and*

*(b) detecting hybridization between the oligonucleotide and the nucleic acid to determine a nucleotide present at one or more of positions 2328, 2338, 2772, 2773 and/or 2784, the identity of the nucleotide indicating whether the HIV sample is sensitive to zidovudine.*

*37. The method of claim 36, wherein the HIV-1 nucleic acid is labeled and the oligonucleotide is unlabeled.*

*38. The method of claim 36, wherein the oligonucleotide includes position 2328 of the HIV-1 reverse transcriptase sequence or its complement and hybridization of the oligonucleotide to the sequence or its complement determines the nucleotide occupying position 2328.*

*39. The method of claim 36, wherein the oligonucleotide includes position 2338 of the HIV-1 reverse transcriptase sequence or its complement and hybridization of the oligonucleotide to the sequence or its complement determines the nucleotide occupying position 2338.*

*40. The method of claim 36, wherein the oligonucleotide includes position 2772 of the HIV-1 reverse transcriptase sequence or its complement and hybridization of the oligonucleotide to the sequence or its complement determines the nucleotide occupying position 2772.*

*41. The method of claim 36, wherein the oligonucleotide includes position 2773 of the HIV-1 reverse transcriptase sequence or its complement and hybridization of the oligonucleotide to the sequence or its complement determines the nucleotide occupying position 2773.*

*42. The method of claim 36, wherein the oligonucleotide includes position 2784 of the HIV-1 reverse transcriptase sequence or its complement and hybridization of the oligonucleotide to the sequence or its complement determines the nucleotide occupying position 2784.*

*43. The method of claim 36, wherein the nucleic acid is isolated by amplifying HIV-1 RNA by RT-PCR.*

*44. The method of claim 36, wherein the nucleic acid is isolated by amplifying HIV-1 DNA by PCR.*

*45. The method of claim 43, wherein the amplifying is performed through the use of nested primers.*

*46. The method of claim 44, wherein the amplifying is performed through the use of nested primers.*

*47. The method of claim 36, wherein the patient has been treated with zidovudine prior to performing step (a).*

*48. The method of claim 36, wherein the patient has not been treated with zidovudine prior to performing step (a).*

* * * * *